US008574166B2

(12) United States Patent
Carr

(10) Patent No.: US 8,574,166 B2
(45) Date of Patent: Nov. 5, 2013

(54) DUAL MODE INTRACRANIAL TEMPERATURE DETECTOR

(75) Inventor: Kenneth L. Carr, Woolwich, ME (US)

(73) Assignee: Meridian Medical Systems, LLC, Portland, ME (US)

( * ) Notice: Subject to any disclaimer, the term of this patent is extended or adjusted under 35 U.S.C. 154(b) by 0 days.

(21) Appl. No.: 13/228,573

(22) Filed: Sep. 9, 2011

(65) Prior Publication Data
US 2012/0029381 A1 Feb. 2, 2012

Related U.S. Application Data

(62) Division of application No. 11/773,056, filed on Jul. 3, 2007, now Pat. No. 8,062,228.

(51) Int. Cl.
*A61B 5/00* (2006.01)
(52) U.S. Cl.
USPC .............................. 600/549; 600/407; 606/101
(58) Field of Classification Search
USPC .................... 600/549, 407; 607/101
See application file for complete search history.

(56) References Cited

U.S. PATENT DOCUMENTS

| | | | |
|---|---|---|---|
| 3,265,993 A * | 8/1966 | Davidson et al. | 333/1 |
| 4,647,281 A * | 3/1987 | Carr | 604/503 |
| 5,461,394 A * | 10/1995 | Weber | 343/786 |
| 5,549,639 A * | 8/1996 | Ross | 607/101 |
| 2003/0067367 A1* | 4/2003 | Volman | 333/125 |
| 2004/0183620 A1* | 9/2004 | Scorer | 333/26 |

OTHER PUBLICATIONS

Stec Multifrequency Microwave Thermograph for Biomedical Applications as submitted by applicant in U.S. Appl. No. 11/773,056.*
Hand et al. "MOnitoring of deep brain temperature in infants using multi-frequency microwave radiometry and thermal modelling" phyiscs in medicine and biology, 2001. pp. 1885-1888.*

* cited by examiner

*Primary Examiner* — Max Hindenburg
*Assistant Examiner* — Renee Danega
(74) *Attorney, Agent, or Firm* — Cesari and McKenna, LLP

(57) ABSTRACT

Apparatus for detecting thermal radiation emanating from two different intracranial depths in a patient includes a transducer having a surface for placement against the patient's cranium. The transducer includes a first antenna with an aperture adjacent that surface the antenna being tuned to a first frequency and producing a first signal indicative of thermal radiation received within an antenna pattern extending a first distance from the surface and a second antenna having a second aperture adjacent to that surface within the first aperture. The second antenna is tuned to a second frequency and produces a second signal indicative of radiation received within an antenna pattern extending a selected second distance from the working surface, the second distance being shorter than the first distance. The two signals are coupled to a receiver/control unit which thereupon monitors and displays the temperature at the two intracranial depths.

28 Claims, 8 Drawing Sheets

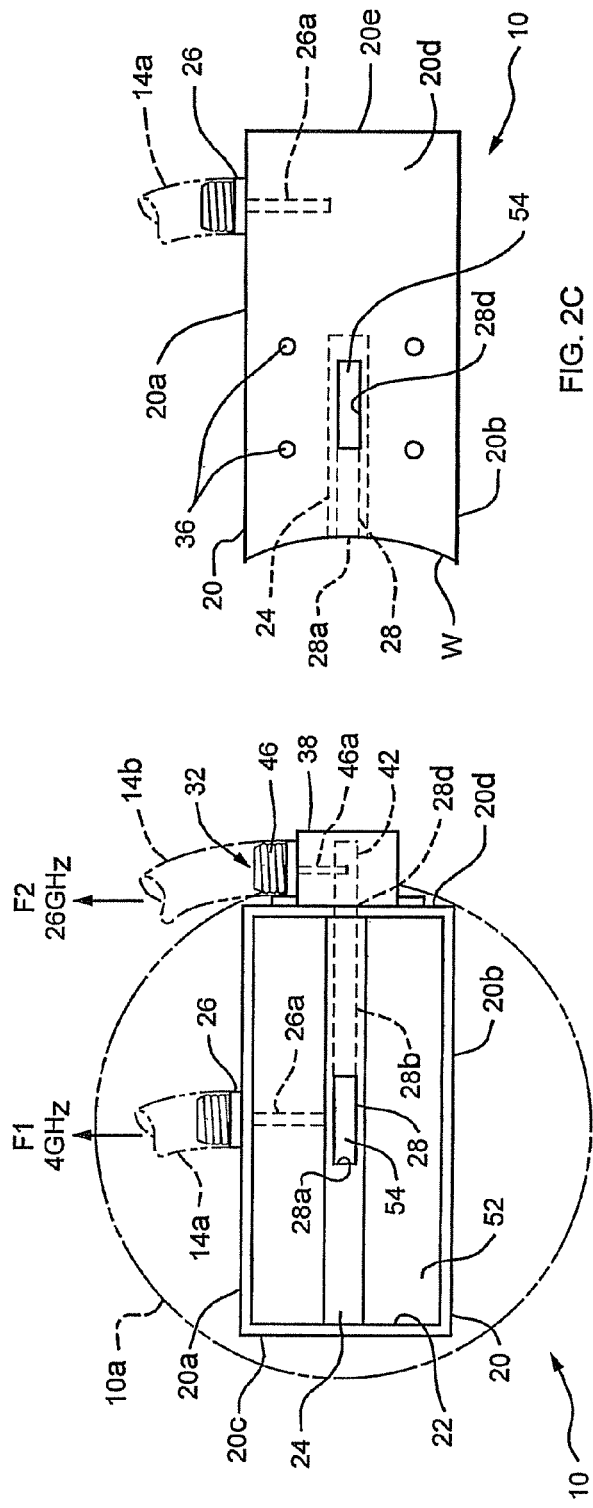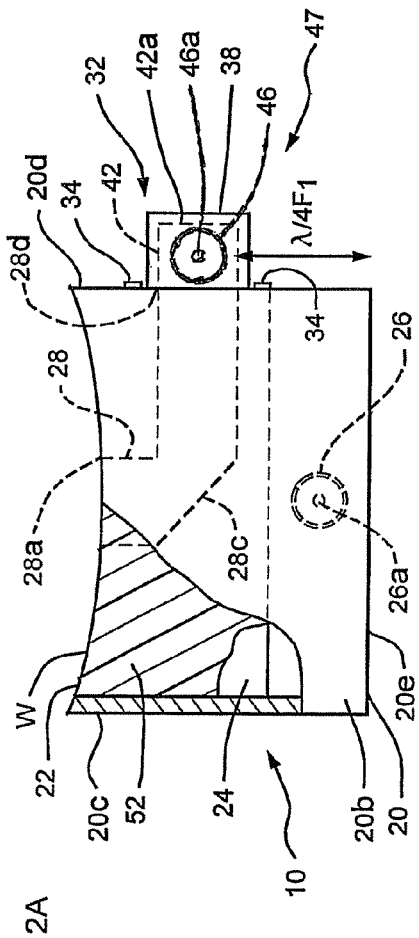

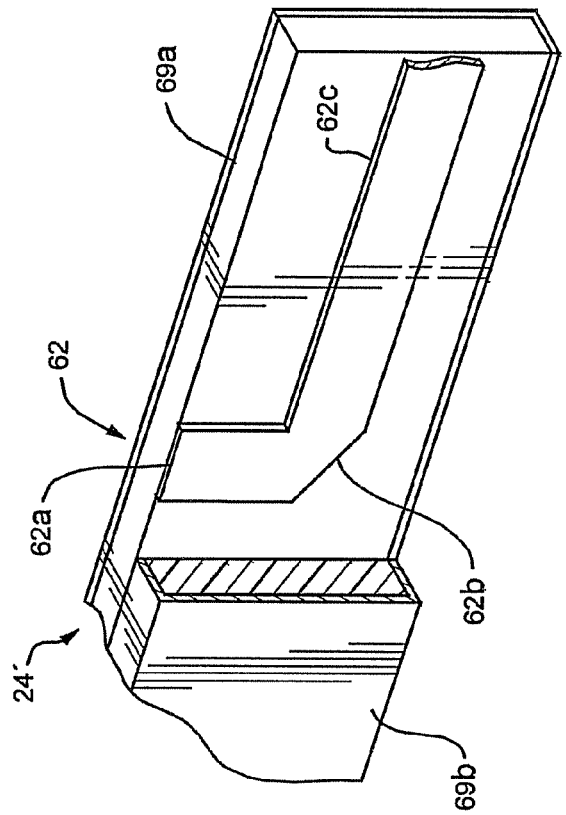
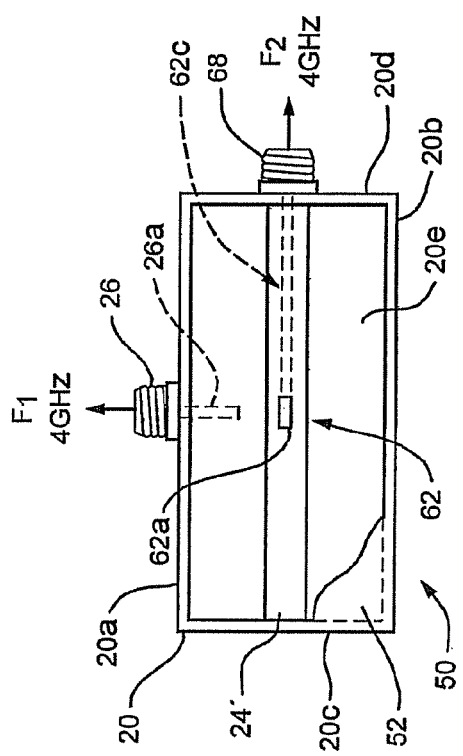
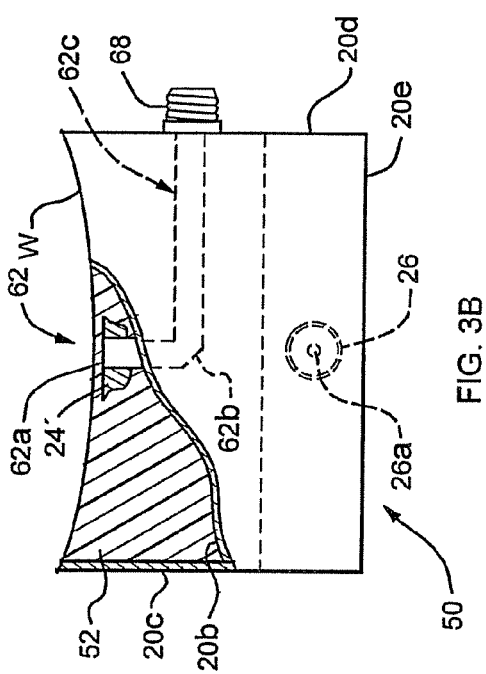

DUAL MODE INTRACRANIAL TEMPERATURE DETECTOR

CROSS-REFERENCE TO RELATED APPLICATION

This application is a division of Ser. No. 11/773,056 filed on Jul. 3, 2007, now U.S. Pat. No. 8,062,228.

BACKGROUND OF THE INVENTION

1. Field of the Invention

This invention relates to temperature monitoring apparatus using microwave radiometry. It relates more particularly to apparatus for non-invasively and reliably detecting and monitoring the temperature of target brain tissue especially in neonatal patients.

2. Background Information

Hypoxic-ischemia or asphyxia is a serious problem in newborns. Lack of an adequate supply of oxygenated blood to the brain may result in serious brain injury called hypoxic-ischemic encephalopathy (HIE). It is estimated that HIE occurs in about 3-9 newborns out of 1,000 term infants. About half of these infants with HIE (range of 35-50%) will die or suffer from severe handicaps such as mental retardation or cerebral palsy.

At the present time, beyond the initial care given to the newborn in the delivery room to provide artificial breathing or medications, there is no standard care to lessen HIE. Multi-centered trials are currently underway in the United States and elsewhere to measure the safety and efficacy of hypothermia in reducing brain injury events following periods of low oxygen to the brain. The objective is to cool the brain by 4-33° with an accuracy of about 0.20° C. Sorely needed, then, is a non-invasive sensor which can reliably detect and monitor temperature of the target brain tissue.

Currently, trials effecting hypothermic cooling of the head or systemic hypothermia utilize rectal temperature as an indirect index of the infant's brain temperature. However, while performing hypothermia, it is necessary not only to control brain temperature but also to control the rate of cooling, as well as the rate to re-warm the brain. Such close control cannot be maintained by measuring temperature at a remote site such as the rectum.

It is also possible to measure deep brain temperature non-invasively using magnetic resonance spectroscopy, but the cost and feasibility are big problems with this approach considering the need for continuous 72-hour thermal monitoring of each newborn in a ferromagnetic-free environment, followed by a 16-24 hour re-warming period, bringing the total time for each hypothermia procedure to about 96 hours.

The monitoring of auxiliary esophageal and nasopharyngeal temperatures to indicate intracranial temperature has also been considered. However, these areas like the rectal area are slow in indicating thermal trends in the brain.

There are also available devices based on infrared (IR) technology which may be placed in the ear. The tympanic membrane temperature is considered a more reliable indicator of brain temperature than oral or rectal readings because it is closer to the brain. However, these so-called tympanic devices, although relatively inexpensive, are still not considered sufficiently accurate for this application. This is because such devices show an inability to deliver an accurate temperature reading for various reasons such as wax and moisture in the ear which are absorptive at IR frequencies. Also, such devices actually measure radiation from the ear canal wall and the environment within the ear canal resulting in a lower temperature reading than would be obtained from the tympanic membrane itself. Still further, the available IR devices are physically large and therefore not suited for the ear of a neonatal patient who, as noted above, may require continuous monitoring for many hours. Finally, commercially available IR devices do not read below 34° C., while the preferred temperature range for intracranial cooling is 32.8-33.0° C.

In sum, the prior apparatus are disadvantaged in that they do not measure the brain parenchymal tissue directly but rather rely on indirect temperature measurements on other parts of the body and they do not also measure the surface temperature at the cranium thereby allowing the patient's skin to be over-cooled during the hypothermic treatment.

Accordingly, it would be desirable to provide apparatus for reliably detecting and monitoring brain temperature at depth as well as near surface temperature directly but non-invasively during long-term hypothermic treatment to reduce the incidence of brain injury particularly in neonates.

SUMMARY OF THE INVENTION

Accordingly, it an object of the present invention to provide apparatus for directly detecting and routinely monitoring intracranial temperature non-invasively in patients, particularly neonates, using microwave radiometry.

Another object of the invention is to provide such apparatus which measures not only intracranial temperature at depth but also surface temperature to prevent the patient's skin from getting too cold during hypothermic treatment.

A further object of the invention is to provide apparatus of this type incorporating a miniature dual mode transducer which may be affixed easily to the head of an infant or neonate.

Yet another object is to provide such a transducer which, while being used over a long period, does not cause discomfort to the patient.

Still another object of the invention is to provide such apparatus in which at least part of the associated radiometric receiver may be integrated into the transducer that is affixed to the patient.

Another object of the invention is to provide apparatus of this type which includes a disposable radiometer coupling device to provide a sterile and intimate interface between the transducer and the patient's skin.

An additional object is to provide apparatus such as this which includes provision for ensuring the effectiveness of the coupling of the transducer to the patient.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, the present apparatus comprises a miniature dual mode transducer containing a pair of antennas capable of detecting the near surface temperature of a patient's cranium as well as the temperature at depth therein. By "near surface temperature" it is meant the temperature of the tissue between the skull and the skin surface which, based on available data, is approximately 2 mm. By "temperature at depth" it is meant the temperature of brain parenchymal tissue at a depth of at least 15 mm. Preferably, the transducer is quite small so that it can be affixed easily to the head of a neonate and remain there for a prolonged period without causing discomfort to the patient.

The present transducer for the measurement of brain temperature is, basically, an aperture shared by two antennas.

One antenna is used to measure temperature at depth, while the second antenna is used to measure temperature at or near the surface. The second antenna may be located in a septum which bisects the aperture. The introduction of the septum has been found to have little, if any, effect on the receive pattern of the aperture. The determination of surface temperature may be displayed by an associated display as "surface" or "skin temperature", but this data may also be used to enhance the ability of the apparatus to predict temperature at depth.

The apparatus may also incorporate a disposable coupler which provides an intimate sterile interface between the transducer and the patient's skin. This ensures that the transducer is positioned properly on the patient's head with no air gaps between it and the patient's skin so that electromagnetic radiation passes efficiently between the head and the transducer.

Finally, the apparatus may include a radiometric receiver/control unit which responds to the dual outputs from the transducer to provide indications of the near surface temperature and the temperature at depth. As we shall see, at least parts of the receiver/control unit may be incorporated into the transducer and the unit may include a unique noise injection reflectometer which provides a measure of the quality of placement of the transducer against the patient's head.

The dual mode transducer may have antennas of various forms. One transducer embodiment comprises a waveguide antenna tuned to a first frequency. The waveguide is partitioned internally by a septum containing a second waveguide antenna tuned to a second, higher, frequency, the two antennas being capable of detecting thermal radiation reflecting the temperature at depth and the near surface temperature, respectively. A second transducer embodiment includes a similar waveguide with septum but has a small antenna in the septum which is tuned to the same frequency as the waveguide in order to detect the two temperatures. A third version of the dual mode transducer is of a triaxial construction. It comprises a relatively large diameter outer coaxial cable antenna tuned to a first frequency with a waveguide transducer within the center conductor of the cable, the waveguide being tuned to a second, higher, frequency to detect the two aforesaid temperatures. A fourth transducer version also includes an outer coaxial cable antenna but with a smaller inner antenna in the center conductor of the larger antenna, both antennas being tuned to the same frequency.

When coupled to a radiometric receiver/control unit, all of the above transducer embodiments enable the reliable and continuous long term detection and monitoring of near surface temperature and temperature at depth in a patient's cranium.

BRIEF DESCRIPTION OF THE DRAWINGS

For a fuller understanding of the nature and objects of the invention reference should be made to the following detailed description taken in connection with the accompanying drawings, in which:

FIG. 2A is a bottom view of a dual mode transducer comprising the FIG. 1 apparatus;

FIG. 2B is a front view with parts broken away thereof;

FIG. 2C is a side view thereof;

FIG. 3A is a bottom view of a second embodiment of the transducer;

FIG. 3B is front view with parts broken away thereof;

FIG. 3C is a fragmentary perspective view with parts broken away on a larger scale showing a part of the FIG. 3A transducer in general detail;

DETAILED DESCRIPTION OF ILLUSTRATIVE EMBODIMENTS

Figure 1:
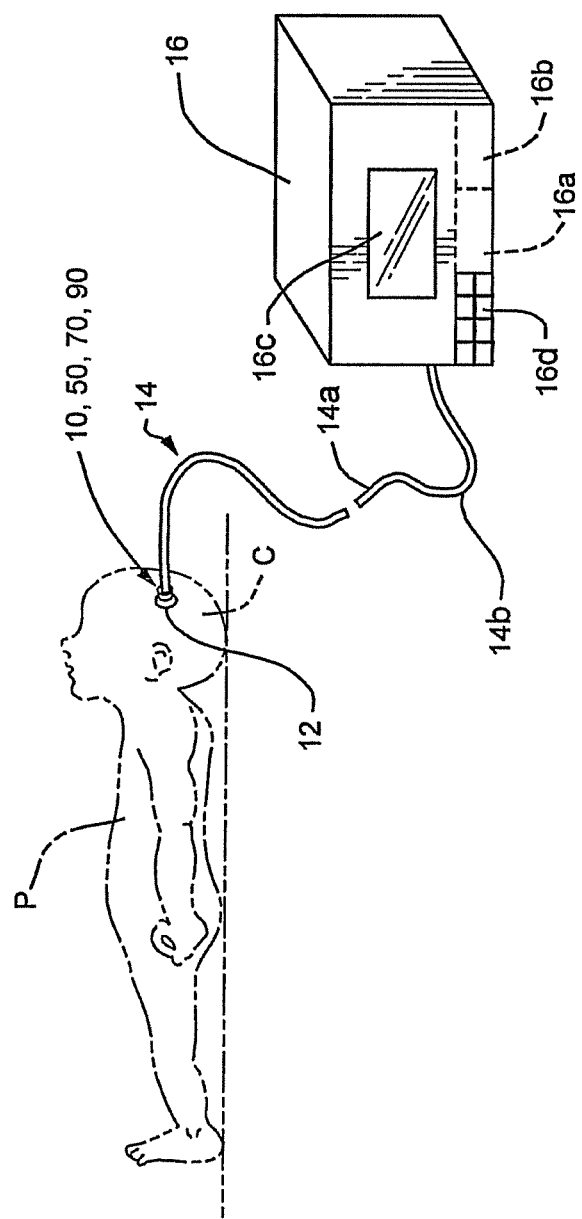
FIG. 1 is a diagrammatic view of a dual mode temperature monitoring apparatus incorporating the invention.

Referring to FIG. 1 of the drawings, my apparatus includes a dual-mode transducer shown generally at 10 which may be removeably affixed to the cranium C of a patient P such as a neonate. Preferably, a conformable coupling member 12 is interposed between the transducer 10 and the patient's skin to provide an intimate coupling between the two which is substantially devoid of air gaps. As we shall see, transducer 10 contains a pair of microwave antennas capable of detecting thermal radiation originating from two different depths in the patient's cranium and producing corresponding output signals which are coupled via a cable 14 to a receiver/control unit 16. That unit includes a radiometric receiver 16a which, under the control of a controller 16b, produces output signals which reflect two intracranial temperatures in the patient P, namely, the temperature at depth, and the near surface temperature. Unit 16 may also include a display 16c which responds to those signals to provide a visible indication of the two temperatures. Display 16c may also display other parameters such as the date and start time of the hypothermic procedure, elapsed time, ambient temperature, patient's pulse rate, apparatus diagnostics, etc. Unit 16 may be turned on and off and controlled by way of a keypad 16d. As we shall see later, in some embodiments of the apparatus, the receiver 16a may be incorporated right into the transducer.

Referring now to FIGS. 2A-2C, transducer 10 may comprise a first antenna in the form of a generally rectangular waveguide 20 composed of a pair of minor-image broader walls 20a and 20b, a pair of mirror-image narrower walls 20c and 20d and an end or rear wall 20e. Spaced opposite the end wall 20e is a front opening or aperture 22 which is bounded by the edges of walls 20a-20d. The aperture and its boundary constitutes the working surface W of the transducer and it may be slightly concave as shown in FIGS. 2B and 2C so that it more or less follows the curvature of the patient's cranium.

In accordance with the invention, waveguide 20 includes a septum 24 which extends between walls 20c and 20d so as to partition aperture 22. The septum essentially bifurcates the waveguide 20 with little if any impact on the antenna pattern of the waveguide. Preferably the septum 24 extends from the working surface W toward end wall 20e a distance that allows for a coaxial connector 26 to be mounted to wall 20a so that its probe 26a can extend into waveguide 20 a sufficient distance to provide a waveguide-to-conductor transition that can couple electromagnetic energy to and from the waveguide 20.

In accordance with the invention, a second antenna in the form of a second, much smaller, waveguide 28 is present in septum 24. As best seen in FIG. 2B, the two waveguides are coaxial and waveguide 28 has an aperture 28a and extends down into septum 24 where it connects to a lateral waveguide segment 28b via a compact H plane right angle bend 28c. Segment 28b extends along septum 24 to a port 28d formed in the waveguide wall 20d. It is apparent, then, that the depth of septum 24 in waveguide 20 should be greater than the length of waveguide aperture 28a so that the septum can accommodate waveguide segment 28b.

As depicted in FIGS. 2A and 2B, the transducer 10 also includes a transition unit 32 which may be mounted to the waveguide wall 20d by threaded fasteners 34 turned down into threaded holes 36 in that wall. Unit 32 has been removed in FIG. 2C so that the holes 36 are visible there.

The transition unit 32 comprises a housing 38 in which there is formed a waveguide extension 42 having an entrance aligned with port 28d in the waveguide wall 20d. The waveguide extension 42 includes an end wall 42a spaced opposite port 28d and which constitutes an end wall for the waveguide 28 as a whole. A coaxial connector 46 is mounted to the side of housing 38 so that its center conductor or probe 46a projects into waveguide extension 42 adjacent to its end wall 42a. Thus, electromagnetic energy may be coupled to and from waveguide 28 via the transition unit 32.

In accordance with the invention, the waveguides 20 and 28 are tuned to two different frequencies. More particularly, waveguide 20 operates at a relatively low frequency $F_1$, e.g. 4 GHz. Consequently, it has a relatively large antenna pattern $A_1$ (FIG. 6C) which extends an appreciable distance from the waveguide aperture 22 and the working surface W, i.e. at least 15 mm. On the other hand, waveguide 28 is tuned to a much higher frequency $F_2$, e.g. 26 GHz, so that its antenna pattern $A_2$ (FIG. 6C), which is within the envelope of pattern $A_1$, extends a much shorter distance from surface W, i.e. about 2 mm. In order to minimize the size of a transducer 10 operating at these frequencies, the waveguide 20 is preferably filled with a dielectric material 52 out to surface W. This reduces the waveguide size by the square root of the dielectric constant $\in_r$ of that material. For example, a 4 GHz waveguide 20 having an aperture 22 that is 3.84×1.59 cm may be filled with Delrin® acetal resin having a dielectric constant $\in_r$ of 3.8. This provides a return loss of 15 dB over the typical 3.75 to 4.2 GHz range of a receiver 16a in control unit 16 (FIG. 1). The waveguide 28, operating at 26 GHz, on the other hand, may have an aperture 28a that is 0.13 by 0.38 cm and be filled with Teflon® tetrafluoroethylene resin having a dielectric constant of 2.1. This antenna provides a return loss of 20 dB for a receiver 16a having a frequency range of 25 to 27 GHz.

In order to separate the two different frequency signals from the waveguide antennas, the probe 46a is spaced from the end wall 20e of waveguide 20 a distance equal to a quarter wavelength (or integral multiple thereof) at the frequency $F_1$. This forms a quarter wave diplexer 47 as shown in FIG. 2B that is integrated into transducer 10.

If desired, the waveguide 20 may be mounted within a circular base or flange as shown in phantom at 10a in FIG. 2A so that the transducer has the general shape of a large aspirin tablet that can be affixed easily to the cranium C of the patient P as shown in FIG. 1.

The cable 14 depicted in that same figure actually comprises a pair of coaxial cables 14a and 14b releasably connected to connectors 26 and 46, respectively. As will be described in more detail later, cables 14a and 14b couple the two output signals $F_1$ and $F_2$ from transducer 10 to a pair of radiometers in receiver 16a of receiver/control unit 16 to provide the temperature at depth and near surface temperature indications that are displayed by that unit's display 16c.

Refer now to FIGS. 3A to 3C which illustrate a second transducer embodiment shown generally at 50 for use in the FIG. 1 apparatus. This embodiment incorporates two antennas tuned to the same frequency, but which are still able to detect the near surface temperature and the temperature at depth in the patient's cranium C. One, outer, antenna in transducer 50 is a waveguide 20 that may be identical to the one described in connection with FIGS. 2A-2C, except that it has a septum 24' that contains, as a second, inner antenna, a stripline 62 having an open end that constitutes an antenna aperture 62a in the middle of the septum at working surface W.

The stripline segment 62 extends down into septum 24' where it transitions via a right angle bend 62b to a lateral segment 62c connected to a SMA connector 68 (e.g. Tensolite™ 5678-5CC) mounted to the wall 20d of waveguide 20.

In this embodiment 50, the two antennas, i.e. waveguide 20 and stripline 62, may operate at the same frequency, i.e. $F_1=F2=4$ GHz, with the stripline 62 having a shorter antenna pattern than that of the waveguide 20 by virtue of its much smaller aperture 62a. In some applications, the antenna in septum 24' may be a coaxial antenna instead of a stripline.

As with the first transducer embodiment 10, the two antennas are coupled by cable 14 to receiver/control unit 16. However, since they operate at the same frequency, their outputs may be time shared with a single radiometer in receiver 16a of unit 16 to be described, enabling the unit 16 to display the near surface temperature and the temperature at depth in the patient's cranium C. For the same reason, transducer 50 does not require a diplexer.

The septum 24' in transducer 50 may actually comprise two circuit boards 69a and 69b positioned side by side as shown in FIG. 3C, the thickness of the boards being exaggerated for clarity. Actually, each circuit board is only in the order of 0.32 inch thick with copper cladding 70 (0.007 inch) on the outboard face and perhaps some edges of the boards to constitute a ground plane. The stripline 62 is printed on circuit board 69a as a copper trace having a thickness of about 0.007 inch. Preferably, the circuit boards 69a, 69b are Duroid™ boards having a dielectric constant of 10.

Figure 4A:
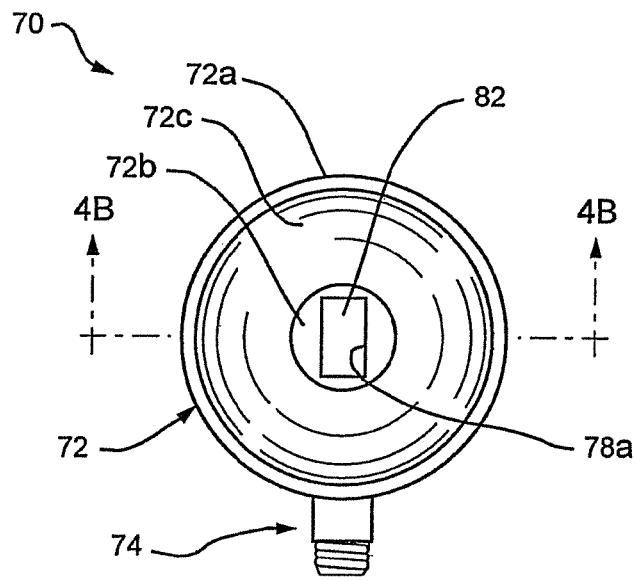
FIG. 4A is a bottom view of a third embodiment of the dual mode transducer.
Figure 4B:
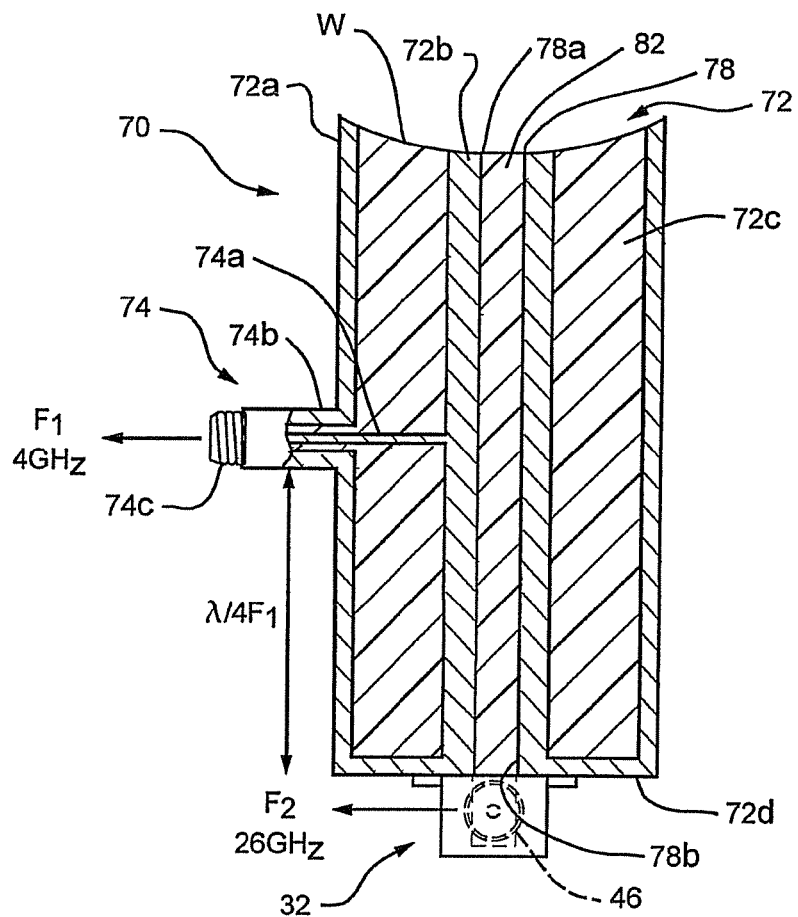
FIG. 4B is a sectional view taken along line 4B-4B of FIG. 4A.

Refer now to FIGS. 4A and 4B which illustrate a third transducer embodiment shown generally at 70. In FIG. 4B, the length of the device is exaggerated for ease of illustration. This embodiment includes a first antenna comprising a coaxial cable segment 72 having an outer conductor 72a and an inner conductor 72b separated by the usual dielectric material 72c. The cable segment 72 extends from a coaxial aperture at working surface W to a short-circuiting end wall 72d spaced from that aperture. It is tuned to frequency $F_1$. The temperature at depth signal detected by antenna 72 is outputted by a coaxial transmission line 74 consisting of a first conductor 74a connected to inner conductor 72b and a second conductor 74b connected to outer conductor 72a, the transmission line ending in a connector 74c.

In accordance with the invention, conductor 72b contains a second, coaxial, antenna comprising a length of waveguide 78 which extends from an aperture 78a at working surface W to a port 78b in end wall 72d. Preferably, the waveguide 78 is filled with a dielectric material 82 to minimize the size of the waveguide as described above. In order to output the signal from waveguide 78, a transition unit 32 similar to the one described above in connection with transducer 10 is mounted to the end wall 72*d* opposite the waveguide port 78*b*. The output from unit 32 present at its connector 46 is a signal $F_2$, e.g. 26 GHz, corresponding to the near surface temperature detected by the transducer 70. As with the transducer 10, the transmission line 74 is spaced from end wall 72*d* a distance corresponding to a quarter wavelength (or integral multiple thereof) at frequency $F_1$. The coaxial portion of antenna 72 and line 74 forms a stub support which achieves a right angle bend. The waveguide 78 continues on to transition 32 forming a quarter wave stub. This structure thus constitutes a diplexer that serves to separate the two output signals $F_1$ and $F_2$. The operation of the transducer is thus similar to that of transducer 10.

Figure 5A:
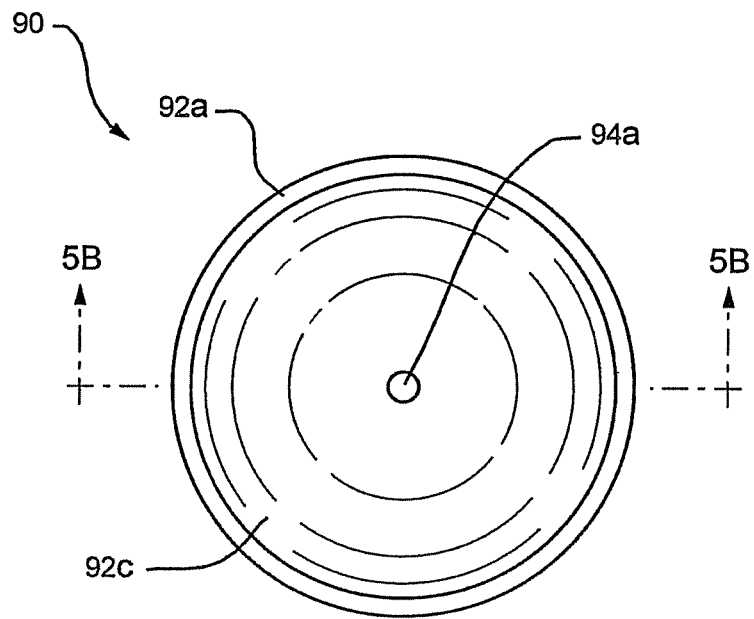
FIG. 5A is bottom view of a fourth embodiment of the transducer.
Figure 5B:
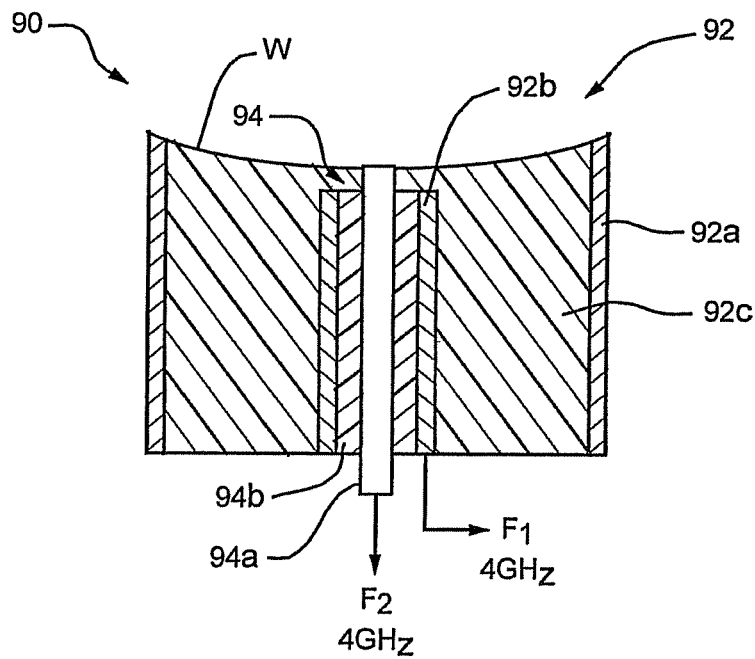
FIG. 5B is a sectional view taken along line 5B-5B of FIG. 5A.

In FIGS. 5A and 5B, a fourth transducer embodiment is shown generally at 90. It comprises a pair of outer and inner coaxial cable antennas 92 and 94 arranged in a triaxial configuration. Antenna 92 comprises an outer conductor 92*a*, e.g. 2.03 cm OD, and an inner conductor 92*b*, e.g. 0.79 cm OD, separated by a dielectric material 92*c*. The antenna 94 is contained within the inner conductor 92*b* and is composed of a center conductor 94*a* separated from conductor 92*b* by a dielectric material 94*b*. The coaxial apertures of antennas 92 and 94 are located at the transducer's working surface W. In this embodiment, the two antennas are tuned to the same frequency, e.g. $F_1=F_2=4$ GHz. Due to its relatively large diameter, the antenna 94 has a characteristic antenna pattern which extends in the order of 15 mm from that working surface. The antenna 94, on the other hand, with its much smaller diameter has a characteristic antenna pattern which is within the envelope of the larger pattern but projects only about 2 mm from that surface.

The transducer 90 operates in a manner similar to that of transducer 50. It is advantaged in that it can have a low profile because it does not require a waveguide-to-conductor transition. In addition, it is fully shielded from external radiation sources, e.g. fluorescent lights. Also, since both antennas operate at the same frequency, it requires only one radiometer in the receiver 16*a* of its unit 16 (FIG. 1).

Figure 6A:
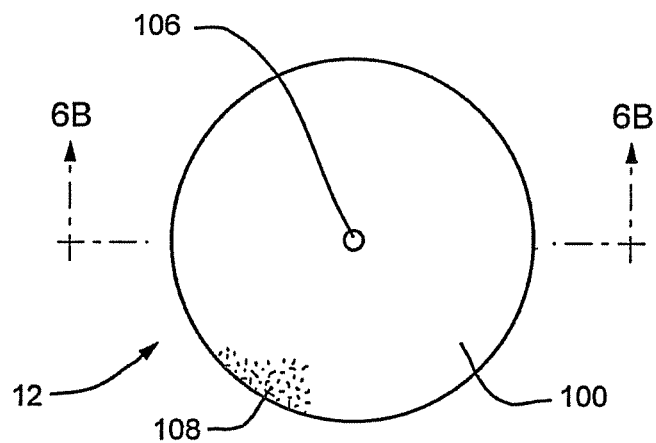
FIG. 6A is a bottom view on a larger scale of the coupler comprising the FIG. 1 apparatus.
Figure 6B:
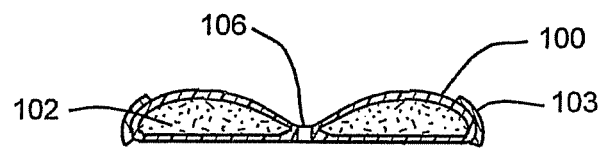
FIG. 6B is a sectional view taken along line 6B-6B of FIG. 6A.
Figure 6C:
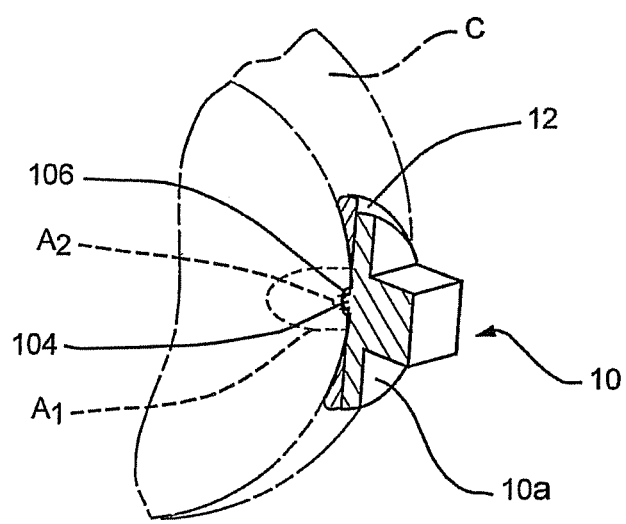
FIG. 6C is a diagrammatic view in section on a much larger scale showing the transducer and coupler in the FIG. 1 apparatus.

Proper placement of the transducers 10, 50, etc. with respect to the patient's cranium C is a primary concern. The coupling member 12 which is shown in detail in FIGS. 6A and 6B helps to accomplish this. Preferably, the coupling member is a disposable sterile article comprising a small, thin wall conformable plastic pouch or bag 100 containing a filler 102 which may be a fluid, a dielectric powder or a combination of both. The coupling member or coupler 12 should have more or less the same size and shape as the transducer working surface W so that it serves as a cushion that conforms to the patient's cranium C and the surface W as shown in FIG. 6C, ensuring that no significant air gaps exist between the two.

The illustrated filler 102 is of titanium dioxide which has a dielectric constant $\in_r$ of approximately 10 in powder form. Such a dielectric constant provides a good transition between the transducer and the patient's skin. This lower constant also reduces the possibility of interference since a lower $\in_r$ will, in essence, reduce (in terms of microwave path) the gap created between the transducer and the cranium by the coupler 12. Adding a slight contour to the working surface W as shown in the drawing figures further reduces this gap.

It is also been found that the $\in_r$ value will be increased with the addition of, for example, mineral oil which has a dielectric constant of 4 coupled with a low loss tangent. This, in essence, displaces any air having an $\in_r$ value of 1 in the pouch 102 with a fluid whose corresponding value is 4. Adding other powders with a lower $\in_r$ will likewise reduce the overall $\in_r$.

Ideally, the thickness of the coupling member 12 at the center of the working surface W should be minimal, e.g. the opposite walls of bag 100 may be welded together at the center of the pouch, with the thickness of the coupler gradually increasing radially so that its outer edge has a thickness in the order of 3.8 mm (based on a typical neonate head diameter of 12.7 cm). In some applications, it may be desirable to metallize the rim of pouch 100 as shown at 103 in FIG. 6B to provide shielding in order to minimize interference from outside radiation sources. Also, if a filler 102 in powder form is used, it is important that the powder does not settle out within the pouch 100. To avoid this, the pouch 100 may have a sponge-like interior impregnated with a filler 102 consisting of a fluid-powder combination as above.

As shown in FIG. 6C, the surface W may be formed with a small bump 104 at its center and the pouch 100 may have at its center a corresponding hole 106 with a welded edge so that the bump and hole may interfit to center the coupler with respect to the transducer. Alternatively, the transducer working surface can be formed with a center dimple adapted to receive a bump centered on the coupler to achieve the same objective.

In use, it may be desirable to releasably affix the coupler 12 to the transducer working surface W and/or to the patient's cranium C. This may be accomplished by covering part or all of the outer surface of the pouch 100 with a low tack adhesive as indicated by the stippling 108 in FIG. 6A. Of course, attachment to the patient's cranium could also be accomplished through the use of a surgical dressing such as one sold under the brand name "Op-Site" which is used in many hospital neonate units.

Figure 7:
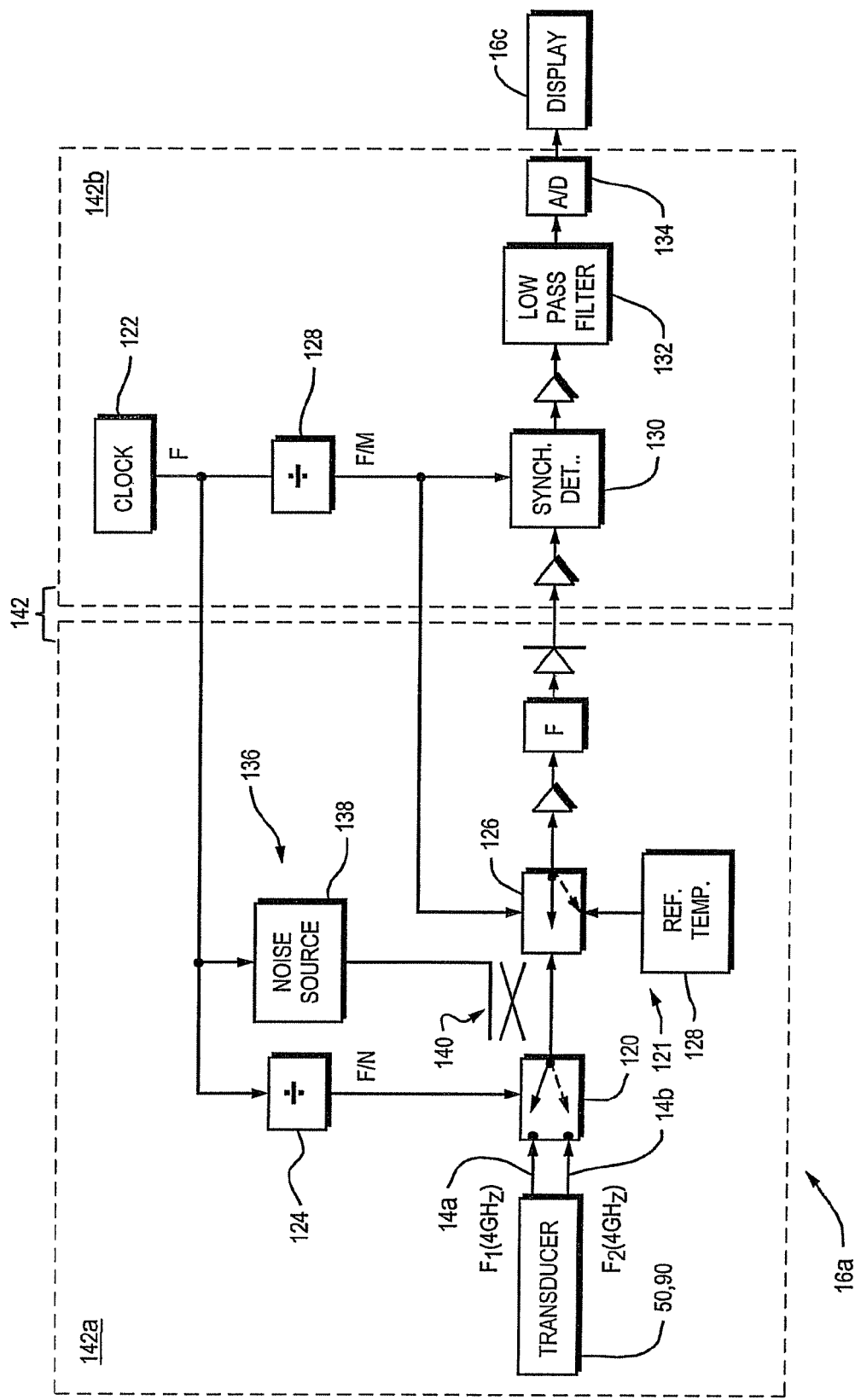
FIG. 7 is a block diagram of a radiometric receiver that may comprise the receiver/control unit in the FIG. 1 apparatus.

As noted above, the two dual mode transducers 50 and 90 are advantaged in that both antennas therein operate at the same frequency, e.g. $F_1=F_2=4$ GHz. Therefore, the receiver/control unit 16 associated therewith requires only one radiometer in receiver 16*a* which may be time shared by the two antennas. Thus, as shown in FIG. 7, the outputs from the two antennas of transducer 50 or 90 may be applied to a receiver 16*a* including a two-position switch 120 followed by a more or less conventional Dicke-type radiometer having a bandwidth that includes 4 GHz and is shown generally at 121. A radiometer of this type is disclosed in my U.S. Pat. No. 4,557,272 whose contents are incorporated by reference herein. That switch may be controlled by signals from a clock 122 which are applied to the switch by way of a divider 124 so as to switch the two transducer outputs to the radiometer at a selected relatively low frequency F/N, e.g. 0.1 Hz.

The alternate signals from switch 120 are applied to one input of the radiometer's Dicke switch 126 which also receives, at a second input, a signal from the radiometer's reference temperature source 128. The Dicke switch may be controlled by signals from clock 122 which are applied to that switch via a divider 128, or more usually by the radiometer directly so that the Dicke switch 126 is switched at a selected much higher frequency F/M, typically 60 Hz. The output from the Dicke switch is amplified and filtered before being applied to the radiometer's synchronous detector 130 that is controlled by the same signals that toggle the Dicke switch 126. The detector output is integrated over a desired period and fed via a low pass filter 132 to an A/D converter 134 whose output may be applied by controller 16*b* to the display 16*c* in control unit 16 so that the display displays the near surface temperature and the temperature at depth detected by the transducer 50 or 90.

It will be appreciated from the foregoing that the larger antenna in each transducer 10, 50, 70, 90 which detects thermal radiation from a brain tissue volume at depth also detects a thermal contribution from the volume near the surface that is sensed by the smaller antenna in each transducer. This is because the smaller antenna pattern $A_2$ is located within the envelope of the larger antenna pattern $A_1$ (FIG. 6C). Preferably, the controller 16b uses the radiometer data associated with the smaller antenna to make a correction to the radiometer data associated with the larger antenna that will compensate for the above near surface volume contribution to the measured temperature at depth to produce a true temperature at depth measurement, i.e. a brain core temperature measurement.

Typical brain temperature behavior as a function of depth may be expressed as follows:

$$T = T_{core} - (T_{core} - T_{surf})e^{(d/cf)} \quad (1)$$

where d=intracranial depth
cf=cooling factor

Using electromagnetic simulations, a transducer depth weighting factor (wf) may be provided which is the fractional contribution of the total received noise power (temperature) by intracranial depth.

The temperature profile may then be integrated over the weighting factor wf as follows:

$$T_{radiometer} = \int_{surface}^{\infty} \{T \times wf\} d \quad (2)$$

to provide an expression for the temperature indication from the total at depth tissue volume. Knowing the near surface temperature and the indicated temperature at depth, the controller 16b can compute the brain core temperature for display by display 16c.

In order to ensure that the transducer and the coupling member 12 are positioned properly on the patient's cranium, the receiver 16a preferably includes a coupler placement monitor in the form of a noise injection reflectometer shown generally at 136 in FIG. 7. The reflectometer comprises a noise source 138 that responds to the signals F from clock 122 to produce wide band microwave noise which is coupled via a coupler 140 onto the radiometer 121 input at Dicke switch 126 and is directed out through the larger antenna in transducer 50 or 90.

The presence of an impedance mismatch due to a poor coupling of the transducer to the patient's cranium C will cause a portion of the noise power to reflect back into the radiometer 121 where it is detected. For example, a return loss of 10 db would correspond approximately to a mismatch of 1.9 to 1 and a 90% transmission. The noise source 138 is toggled on and off by signals F from clock 122 and, in more or less the same way as the Dicke switch 126 compares the input temperature from the transducer to the reference temperature from source 128, the reflected noise is compared to the absence of reflected noise to determine a reflection coefficient. This provides a reflection measurement that may be integrated over the detection bandwidth and weighted by the band limiting characteristics of the radiometer by controller 16b. That reflection measurement may be also displayed by display 16c to apprise the operator of the quality of placement of the transducer on the cranium C.

While the receiver 16a shown in FIG. 7 is contained in the control unit 16, at least some of its components could be incorporated into the associated transducer. In this event, the FIG. 7 receiver may be implemented as a monolithic microwave integrated circuit (MMIC) chip 142. Such a solid state chip is so small that it may be mounted on a transducer wall, e.g. wall 20a in FIG. 3A, or it may be placed in the transducer base 10a (FIG. 2A). In this event, the antenna connectors, e.g. connectors 26 and 68 in FIG. 3A, may be replaced by stripline connections to the chip 142. Also in some cases, the receiver circuit is formed as two separate MMIC chips 142a and 142b as shown in FIG. 7, the former being incorporated into the transducer, the latter being in unit 16. This simplifies manufacture of the overall circuit 142 and minimizes feedback between the chip components.

Figure 8:
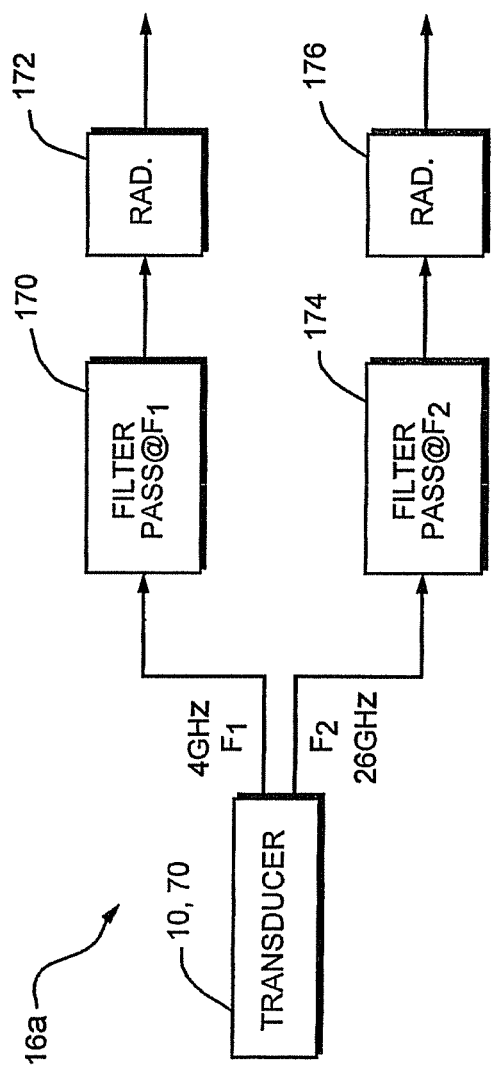
FIG. 8 is a similar diagram of a second receiver embodiment.

In contrast to transducers 50 and 90, the transducers 10 and 70 described above each produce dual outputs at frequencies $F_1$ and $F_2$ that are different. Therefore, the receiver 16a associated with those transducers requires two radiometers as shown in FIG. 8. As seen there, the transducer output signal $F_1$ is coupled to a band pass filter 170 which passes that signal to a radiometer 172 having a bandwidth which includes frequency $F_1$. Similarly, the transducer output signal $F_2$ is fed to a second band pass filter 174 which applies that signal to a second radiometer 176 whose bandwidth includes the frequency $F_2$. The outputs from the two radiometers may then be applied via suitable amplifiers and A/D converters (not shown) to provide input signals for display 16c so that the display indicates the near surface temperature and the temperature at depth sensed by the transducer 10 or 70.

It will be thus seen that the objects set forth at the outset, among those made apparent from the preceding description, are efficiently attained. Also, certain changes may be made in the above constructions without departing from the scope of the invention. For example, in the transducers 10 and 70, the waveguide-to-conductor transition unit 32 may be substituted for by stripline or a waveguide-to-waveguide transition unit that extends to receiver/control unit 16. Therefore, it is intended that all matter contained in the above description or shown in the accompanying drawings shall be interpreted as illustrative and not in a limiting sense.

It is also to be understood that the following claims are intended to claim all of the generic and specific features of the invention described herein.

I claim:

1. Apparatus for detecting thermal radiation emanating from two different intracranial depths in a patient, said apparatus comprising a dual-mode transducer having a working surface for placement against a patient's cranium, said transducer including
   a first antenna extending along an axis to a first end at or adjacent to said working surface, said first antenna having a characteristic first antenna pattern that extends a selected first distance from said working surface and being tuned to a first frequency, said first antenna producing a first output signal indicative of thermal radiation received within said first antenna pattern, and
   a second antenna extending along said axis within the first antenna to a second end adjacent to said working surface, said second antenna being isolated from said first antenna and having a characteristic second antenna pattern that extends a selected second distance from said working surface within the envelope of the first antenna pattern and being tuned to a second frequency, said second antenna producing a second output signal indicative of thermal radiation received within said second antenna pattern, said second distance being appreciably shorter than said first distance.

2. The apparatus defined in claim 1 wherein the first antenna comprises a first coaxial cable including inner and outer conductors extending from said first end to the outside of the transducer to output said first output signal.

3. The apparatus defined in claim 2 wherein said second antenna comprises a transmission line within the inner conductor of the first coaxial cable and extending from said second end to the outside of the transducer to output said second output signal.

4. The apparatus defined in claim 3 wherein the transmission line comprises a center conductor insulated from said inner conductor.

5. The apparatus defined in claim 4 wherein said first coaxial cable and said center conductor are in a triaxial configuration.

6. The apparatus defined in claim 4 wherein said first and second frequencies are substantially the same.

7. The apparatus defined in claim 3 wherein the second antenna comprises a waveguide extending within the inner conductor of said first coaxial cable, said waveguide having an aperture constituting said second end and a side wall extending from said aperture to a closed end spaced from the aperture.

8. The apparatus defined in claim 7 wherein said second frequency is substantially higher than said first frequency.

9. The apparatus defined in claim 7 and further including a transition extending from the waveguide to the outside of the transducer to output said second output signal.

10. The apparatus defined in claim 9 wherein the transition is spaced from said closed end a distance substantially equal to a quarter wavelength or integral multiple thereof at said first frequency.

11. The apparatus defined in claim 10 wherein the transition comprises a waveguide-to-coaxial conductor transition.

12. The apparatus defined in claim 10 wherein said transition comprises a waveguide-to-waveguide transition.

13. The apparatus defined in claim 10 wherein said transition comprises stripline.

14. The apparatus defined in claim 7 wherein the waveguide contains a material having a selected dielectric constant.

15. The apparatus defined in claim 1 wherein said working surface is concave and has a dielectric coating.

16. The apparatus defined in claim 1 and further including a conformable coupling device having a selected dielectric constant and for placement between said working surface and said cranium for coupling electromagnetic energy between the two.

17. The apparatus defined in claim 16 wherein the coupling device comprises a flexible pouch at least partially filled with a dielectric material.

18. The apparatus defined in claim 17 wherein said working surface and said pouch are circular and the pouch is thinner at its center than at its edge.

19. The apparatus defined in claim 18 and further including an electrically conductive coating at the pouch edge.

20. The apparatus defined in claim 17 wherein said working surface and said pouch have interfitting surfaces for centering the pouch on the working surface.

21. The apparatus defined in claim 17 and further including a low tack adhesive outer coating on at least part of the pouch.

22. The apparatus defined in claim 1
wherein said first and second frequencies are substantially the same, and
further including a radiometer having an input and a frequency range encompassing the first and second frequencies, and a switch for switching said first and second output signals alternately to said radiometer input, said radiometer producing alternate outputs indicative of the temperatures at said two different intracranial depths.

23. The apparatus defined in claim 22 wherein the radiometer comprises at least one MMIC mounted to the transducer.

24. The apparatus defined in claim 22 and further including a noise injection reflectometer coupled to said radiometer input.

25. The apparatus defined in claim 1
wherein said first and second frequencies are different, and
further including a first radiometer having an input and a frequency range encompassing said first frequency, said first radiometer receiving at its input said first output signal and producing an indication of the temperature at one of said two intracranial depths and a second radiometer having an input and a frequency range encompassing said second frequency, said second radiometer receiving at its input said second output signal and producing an indication of the temperature at the other of said two intracranial depths.

26. The apparatus defined in claim 25 and further including a noise injection reflectometer coupled to one of said radiometer inputs.

27. Apparatus for detecting thermal radiation emanating from two different depths in a patient, said apparatus comprising a dual-mode transducer having a working surface for placement against a patient's cranium, said transducer including
a first antenna extending along an axis to a first end defining a first aperture at or adjacent said working surface, said first antenna having a characteristic first antenna pattern that extends a selected first distance along said axis from said working surface and being tuned to a first frequency, said first antenna producing a first output signal indicative of thermal radiation received within said first antenna pattern, wherein the transducer also includes
a second antenna extending along said axis to a second end adjacent to said working surface and defining a second aperture which is shared with the first aperture, said second antenna being isolated from the first antenna and having a characteristic second antenna pattern that extends a selected second distance along said axis from said working surface within the envelope of the first antenna pattern and being tuned to a second frequency, said second antenna producing a second output signal indicative of thermal radiation received within said second antenna pattern, said second distance being appreciably shorter than said first distance,
wherein the first antenna comprises a first waveguide having a first aperture constituting said first end,
wherein the first waveguide includes a side wall extending from the first aperture to a closed end spaced from the first aperture, and a septum extending between opposite locations on the side wall so as to partition the first aperture, and
wherein the second antenna extends along said axis within the septum.

28. The apparatus defined in claim 27 wherein the second antenna comprises a second waveguide having a second aperture constituting said second end, and said second frequency is appreciably higher than the first frequency.

* * * * *

UNITED STATES PATENT AND TRADEMARK OFFICE
CERTIFICATE OF CORRECTION

PATENT NO.        : 8,574,166 B2                            Page 1 of 1
APPLICATION NO.   : 13/228573
DATED             : November 5, 2013
INVENTOR(S)       : Kenneth L. Carr It is certified that error appears in the above-identified patent and that said Letters Patent is hereby corrected as shown below:

In the Specification

In col. 4, line 53 should read:
waveguide 20 composed of a pair of ~~minor~~mirror-image broader Signed and Sealed this
Eighteenth Day of February, 2014

Michelle K. Lee
*Deputy Director of the United States Patent and Trademark Office*